United States Patent [19]
Shaffer et al.

[11] Patent Number: 5,880,215
[45] Date of Patent: Mar. 9, 1999

[54] COATINGS WITH IMPROVED RESISTANCE TO SUNTAN LOTION

[75] Inventors: Myron W. Shaffer, Cumberland, W. Va.; Kyli Martin, Bridgeville; Shelley Parkerson-Hoy, Pittsburgh, both of Pa.

[73] Assignee: Bayer Corporation, Pittsburgh, Pa.

[21] Appl. No.: 998,303

[22] Filed: Dec. 24, 1997

[51] Int. Cl.$^6$ .............................. C08J 3/00; C08K 3/20; C08L 75/00

[52] U.S. Cl. ..................... 524/839; 524/539; 524/591; 524/840

[58] Field of Search ................... 524/591, 839, 524/840, 539

[56] References Cited

U.S. PATENT DOCUMENTS

| | | | |
|---|---|---|---|
| 4,745,151 | 5/1988 | Noll et al. | 524/591 |
| 5,387,642 | 2/1995 | Blum et al. | 524/591 |
| 5,731,396 | 3/1998 | Laas et al. | 528/49 |
| 5,741,849 | 4/1998 | Blum et al. | 524/839 |

*Primary Examiner*—Patrick D. Niland
*Attorney, Agent, or Firm*—Joseph C. Gil; Thomas W. Roy

[57] ABSTRACT

The present invention relates to an aqueous coating composition containing prior to the reaction between components A) and B)

A) 10 to 75 wt. %, based on the solids contents of components A) and C), of at least one dispersion or solution of a polyester polyol containing carboxylate and/or sulphonate groups, having a weight average molecular weight of 1,000 to 40,000, an OH number of 15 to 100 and an acid number of 2 to 40 based on all of the carboxylate, carboxyl and sulphonate groups, B) an ester-modified polyisocyanate having an average NCO functionality of 2 to 6 and containing 5 to 20 wt. % of ester groups (calculated as $C_3O_2$, MW 68), 5 to 18 wt. % of isocyanate groups and 0 to 20 wt. % of chemically incorporated hydrophilic, nonionic groups, wherein the preceding percentages are based on the solids content of the ester modified polyisocyanate and C) 25 to 90 wt. %, based on the solids contents of components A) and C), of at least one physically drying, aqueous polyurethane dispersion containing carboxylate and/or sulphonate groups, wherein components A) and B) are present at an NCO/OH equivalent ratio, based on the isocyanate groups of component B) and the hydroxyl groups of component A), of 0.3:1 to 5:1.

The present invention also relates to the coatings prepared from these coating compositions, which have improved resistance to suntan lotion.

8 Claims, No Drawings

COATINGS WITH IMPROVED RESISTANCE TO SUNTAN LOTION

BACKGROUND OF THE INVENTION

1. Field of the Invention

The present invention relates to aqueous compositions containing an ester-modified polyisocyanate, an aqueous polyester resin containing hydroxy groups and optionally urethane groups, and a physically drying, aqueous polyurethane resin, and to coatings prepared from these aqueous compositions which have improved resistance to suntan lotion.

2. Description of the Prior Art

Aqueous polyurethane coating compositions may be used for coating a wide variety of substrates, both rigid and flexible. One use for these compositions is for coating interior parts on automobiles. The coating compositions are based on a water dispersible polyisocyanate, an aqueous polyester urethane polyol and a physically drying aqueous polyurethane resin. The resulting coatings have what is known as a "soft feel," i.e., a leather-like feel.

When they are applied to interior surfaces, such as instrument panels, airbag covers, arm rests or interior door panels, they provide a soft, more desirable feel to these substrates. One of the disadvantages of these coatings is that they do not possess good suntan lotion resistance, which is one of the requirements of automotive manufacturers. Suntan lotion can penetrate through these coatings and cause delamination of the coating from the substrate.

Accordingly, it is an object of the present invention to provide improved coating compositions, which have sufficiently improved resistance to suntan lotion to pass the requirements of automotive manufacturers.

This object can be achieved with the coating compositions according to the present invention that are described hereinafter. It has been found that by incorporating ester groups into the polyisocyanate component, the suntan resistance of the resulting coatings can be improved.

It is disclosed in copending application, U.S. Ser. No. 08/666,166, that blends of physically drying (fully reacted) polyurethanes can be added to blends of two-component aqueous polyurethane coating compositions (a mixture of a water dispersible polyisocyanate and an aqueous polyester urethane polyol) to provide long processing times as well as rapid drying at room temperature. These coatings are particularly useful as wood coatings, e.g., for furniture and parquet flooring. However, this application does not disclose that the resistance to suntan lotion could be improved by modifying the polyisocyanate component in accordance with the present invention.

SUMMARY OF THE INVENTION

The present invention relates to an aqueous coating composition containing prior to the reaction between components A) and B)
A) 10 to 75 wt. %, based on the solids contents of components A) and C), of at least one dispersion or solution of a polyester polyol containing carboxylate and/or sulphonate groups, having a weight average molecular weight of 1,000 to 40,000, an OH number of 15 to 100 and an acid number of 2 to 40, based on all of the carboxylate, carboxyl and sulphonate groups,
B) an ester-modified polyisocyanate having an average NCO functionality of 2 to 6 and containing 5 to 20 wt. % of ester groups (calculated as $C_3O_2$, MW 68), 5 to 18 wt. % of isocyanate groups and 0 to 20 wt. % of chemically incorporated hydrophilic, nonionic groups, wherein the preceding percentages are based on the solids content of the ester modified polyisocyanate and
C) 25 to 90 wt. %, based on the solids content of components A) and C), of at least one physically drying, aqueous polyurethane dispersion containing carboxylate and/or sulphonate groups, wherein components A) and B) are present at an NCO/OH equivalent ratio, based on the isocyanate groups of component B) and the hydroxyl groups of component A), of 0.3:1 to 5:1.

The present invention also relates to the coatings prepared from these coating compositions, which have improved resistance to suntan lotion.

DETAILED DESCRIPTION OF THE INVENTION

Component A) is an aqueous solution or dispersion of a polyester resin containing anionic groups, hydroxy groups and optionally urethane groups. These resins are described, e.g., in copending application, U.S. Ser. No. 08/666,166, and in U.S. Pat. No. 5,387,642, both of which are herein incorporated by reference.

Whether the polyester resins are present as solutions or dispersions depends upon their molecular weight, anionic group content, the type of neutralizing agent and the type and quantity of optional additives such as solvents and emulsifiers. Generally, both dissolved and dispersed components are present.

In the coating compositions according to the invention, component A) is present in an amount of 10 to 75 wt. %, preferably 20 to 65 wt. % and more preferably 25 to 50 wt. %, and component C) is present in an amount of 25 to 90 wt. %, preferably 35 to 85 wt. % and more preferably 50 to 75 wt. %, based on the solids contents of components A) and C). The aqueous solution or dispersion of components A) and C) preferably has a solids content of 15 to 70, more preferably 25 to 45 wt. %.

Component A) is selected from polyester resins containing carboxylate and hydroxyl groups and optionally urethane groups, which are dispersed or dissolved in water, preferably have a weight average molecular weight ($M_w$, determined by gel permeation chromatography using calibrated polystyrene as the standard) of 1,000 to 40,000, more preferably 2,000 to 30,000, and an OH number of 15 to 100, preferably 20 to 75 and an acid number of 2 to 40, preferably 4 to 40 and more preferably 10 to 40. When urethane groups are present, these polyester resins have a urethane group content (calculated as NH—CO—O, MW 59) of 2.5 to 15 wt. %, preferably 5 to 13 wt. %, based on the solids content of the polyester resin.

Component A) is preferably present as a 15 to 70, more preferably a 25 to 45 wt. % aqueous solution or dispersion, which preferably has a viscosity of 25 to 15,000, more preferably of 75 to 8,000 mPa·s at 23° C. and preferably has a pH of 5 to 10, more preferably 6 to 9.

Suitable carboxylate and hydroxyl group-containing polyesters A) include those based on the reaction product of
A1) 65 to 100 wt. % of one or more polyester precursors prepared from
A1.a) 0 to 40, preferably 0 to 25 wt. % of one or more monofunctional alcohols or monocarboxylic acids,
A1.b) 20 to 65, preferably 30 to 60% wt. % of one or more di-, tri-, and/or tetra-functional alcohols,
A1.c) 20 to 60, preferably 25 to 55 wt. % of one or more di- and/or trifunctional carboxylic acids or their anhydrides and A1.d) 0 to 20, preferably 0 to 10 wt. % of one or more isocyanate-reactive compounds containing carboxyl or sulphonate groups, A2) 0 to 8 wt. % of one or more mono-, di- and/or trifunctional compounds containing hydroxyl and/or amino groups other than those of component A4), A3) 0 to 22 wt. % of one or more di- or polyisocyanates and A4) 0 to 15 wt. % of one or more isocyanate-reactive compounds containing carboxyl or sulfonate groups.

Preferably, the percentages of A1) to A4) and A1.a) to A1.d) add up to 100% in each case. In addition, it is preferred to incorporate components A2) and A4) into polyester A) rather than for these components to be present in physical admixture with component A1). Therefore, if component A3) is not present, then components A2) and A4) are also not present.

Starting component A1.a) is based on at least one monocarboxylic acid having a molecular weight of 112 to 340. Examples of suitable monocarboxylic acids include benzoic acid, tert-butylbenzoic acid, hexahydrobenzoic acid, saturated fatty acids such as 2-ethylhexanoic acid, isononanoic acid, coconut oil fatty acid, hydrogenated commercial fatty acids and fatty acid mixtures (e.g., the saturated $C_{14}$–$C_{20}$-fatty acid mixtures, available as Prifac 7900, Prifac 2960 or Prifac 2980 from Unichema International), decanoic acid, dodecanoic acid, tetradecanoic acid, stearic acid, palmitic acid, docosanoic acid, unsaturated fatty acids such as soya bean oil fatty acid, castor oil fatty acid, sorbic acid, ground nut oil fatty acid, conjuenic fatty acid, tall oil fatty acid, safflower oil fatty acid and mixtures of these or other monocarboxylic acids. Preferred monocarboxylic acids include benzoic acid, 2-ethylhexanoic acid, Prifac 2960 fatty acid mixture and soya bean oil fatty acid.

Suitable monohydric alcohols are those having a molecular weight of 100 to 290, such as n-hexanol, cyclohexanol, decanol, dodecanol, tetradecanol, octanol, octadecanol, natural fatty alcohol mixtures (e.g., Ocenol 110/130, available from Henkel) and mixtures of these and other alcohols.

Suitable components A1.b) include diols, triols and higher functionality alcohol components having a molecular weight of 62 to 400, preferably 62 to 192. Examples include ethylene glycol, 1,2- and 1,3-propylene glycol, 1,3-, 1,4- and 2,3-butanediol, 1,6-hexanediol, 2,5-hexanediol, trimethylhexanediol, diethylene glycol, triethylene glycol, hydrogenated bisphenols, 1,4-cyclohexane diol, 1,4-cyclohexane dimethanol, neopentyl glycol, tricyclodecane diol, trimethylolpropane, glycerol, pentaerythritol, trimethylpentane diol, dipentaerythritol and mixtures of these or other polyvalent alcohols. Preferred components A1.b) include ethylene glycol, 1,2-propanediol, 1,6-hexanediol, 1,4-cyclohexane dimethanol, diethylene glycol, neopentyl glycol and trimethylol propane.

Starting component A1.c) is based on di- and/or tricarboxylic acids or their anhydrides having a molecular weight of 98 to 600, preferably 98 to 540. Examples include phthalic acid (anhydride), isophthalic acid, terephthalic acid, tetrahydrophthalic acid (anhydride), hexahydrophthalic acid (anhydride), maleic acid (anhydride), succinic acid (anhydride), fumaric acid, adipic acid, sebacic acid, azelaic acid, dimeric fatty acids, trimeric fatty acids, trimellitic acid (anhydride) and mixtures of these or other acids. Preferred components A1.c) include phthalic acid anhydride, isophthalic acid, terephthalic acid, 1,3- and 1,4-hexahydrophthalic acid anhydride, adipic acid and dimeric fatty acid.

Starting component A1.d) is based on hydroxycarboxylic acids, lactones, aminoalcohols and/or aminocarboxylic acids, e.g., dimethylolpropionic acid, lactic acid, maleic acid, tartaric acid, ε-caprolactone, aminoethanol, aminopropanol, diethanolamine, aminoacetic acid and aminohexanoic acid.

The manufacture of polyesters A1) from A1.a), A1.b), A1.c) and A1.d) takes place, e.g., by a known polycondensation reaction, optionally with the assistance of conventional esterification catalysts, preferably by melt or azeotropic condensation at temperatures of 140° to 240° C. When esterification takes place azeotropically, the entraining agent, which is normally isooctane, xylene, toluene or cyclohexane, may be removed by distillation under vacuum after the reaction.

Suitable components A2) for preparing polyester resins A) include the diols previously set forth for component A1.b), preferably neopentyl glycol, ethylene glycol, butane diol, hexane diol and trimethylol propane; aminoalcohols, preferably ethanolamine, diethanolamine; and diamines such as ethylenediamine.

Component A3) is selected from polyisocyanates having at least two isocyanate groups and having a molecular weight of 140 to 1000. Examples include hexamethylene diisocyanate, 2,4- and/or -4,4'-diisocyanato-dicyclohexylmethane, isophorone diisocyanate, toluylene diisocyanate, diphenylmethane diisocyanate and other isocyanates such as those described in "Methoden der organischen Chemie" (Houben-Weyl, Vol. 14/2, 4th Edition, Georg Thieme Verlag Stuttgart, 1963, pp. 61 to 70).

Also suitable are lacquer polyisocyanates prepared from hexamethylene diisocyanate, isophorone diisocyanate and toluylene diisocyanate and containing, e.g., urethane groups, uretdione groups, isocyanurate, allophanate and/or biuret groups. Mixtures of the previously described polyisocyanates are also suitable.

Preferred polyisocyanates include hexamethylene diisocyanate, isophorone diisocyanate, 2,4'- and 4,4'-diisocyanato-dicyclohexylmethane and polyisocyanate adducts prepared from hexamethylenediisocyanate, such as those mentioned hereinafter in the description of component B). Especially preferred are hexamethylene diisocyanate or isocyanate mixtures which contain at least 50 wt. % of hexamethylene diisocyanate.

Component A4) is selected from isocyanate-reactive compounds containing carboxyl or sulfonate groups, preferably carboxyl groups. Suitable isocyanate-reactive groups include amino and hydroxy groups, preferably hydroxy groups. These compounds are known and disclosed in U.S. Pat. Nos. 3,479,310, 4,108,814 and 4,408,008, herein incorporated by reference.

Component A4) is preferably a 2,2-bis-(hydroxy-methyl)-alkane-carboxylic acid having a total of at least five carbon atoms, preferably 2,2-bis-(hydroxymethyl)-propionic acid (dimethylolpropionic acid) or a t-amine salt of such an acid, for example, the triethyamine salt of dimethylolpropionic acid.

Polyesters A1) are optionally reacted with components A2), A3) and/or A4) at 60° to 160° C. This reaction can be carried out in the absence of solvents or in the presence of an inert organic solvent with the optional assistance of suitable urethane catalysts.

Suitable organic solvents for manufacturing polyester resins A) include N-methyl pyrrolidone, diethylene glycol dimethyl ether, methyl ethyl ketone, methyl isobutyl ketone, acetone, xylene, toluene, butyl acetate, methoxypropyl acetate and mixtures of these or other solvents. The organic solvents may be completely or partially removed from the reaction mixture before, during or after the dispersion step either azeotropically and/or by the application of a vacuum or a stream of inert gas.

Suitable catalysts for the urethanization reaction are known and include tertiary amines such as triethylamine; metallic compounds such as tin(II)octoate, dibutyltin oxide and dibutyltin dilaurate. Suitable catalysts for the esterification reaction include dibutyltin oxide and paratoluenesulphonic acid.

Before or during the dispersion step, if sufficient amounts of salt groups are not present to provide water dispersibility, then preferably 30 to 100, more preferably 50 to 100% of the incorporated acid groups, preferably carboxylic acid groups, are converted to the salt form. A stoichiometric excess of the neutralizing agents may be used.

Examples of suitable bases include ammonia, N-methylmorpholine, triethylamine, dimethylethanolamine, methyidiethanolamine, triethanolamine, morpholine, tripropylamine, ethanolamine, triisopropanolamine, 2-amino-2-methyl-1-propanol and mixtures of these and other neutralizing agents. Sodium hydroxide, lithium hydroxide and potassium hydroxide are also suitable neutralizing agents, but are less preferred. Ammonia, triethyl amine and dimethylethanolamine are preferred neutralizing agents.

After the manufacture of the polyester resins, it is also possible to add small amounts of other organic solvents or reactive thinners (such as ethanol, propanol, ethylene glycol, propylene glycol, butanol, butyl glycol, hexanol, octanol, butyl diglycol, glycerol, ethyl diglycol, methyl diglycol and methoxypropanol) to obtain special properties.

Polyester resins A) may be dispersed in accordance with several embodiments, i.e., a water/neutralizing agent mixture may be added to the resin, water may be added to the resin/neutralizing agent mixture, the resin may be added to the water/neutralizing agent mixture or the resin/neutralizing agent mixture may be added to water. The dispersibility of the resin in water may be improved, if desired, by the additional use of external emulsifiers, such as ethoxylated nonylphenol, during dispersion.

The dispersion step is preferably carried out at 40° to 120° C. The aqueous solutions or dispersions of polyester resins A) preferably have a solids content of 15 to 70, preferably 25 to 45 wt. %. The aqueous resins should not contain solvents and reactive thinners in an amount of more than 8, preferably not more than 6 and more preferably not more than 4 wt. %, based on the weight of the polyester dispersion or solution.

Polyisocyanate component B) is selected from polyisocyanates which have been modified to contain ester groups. The modified polyisocyanates have aliphatically, cycloaliphatically, araliphatically and/or aromatically bound isocyanate groups, preferably aliphatically and/or cycloaliphatically bound isocyanate groups, and may be liquid or solid at room temperature, preferably liquid, and if liquid, have a viscosity of 1000 to 200,000, preferably 1000 to 100,000 and more preferably 3000 to 70,000 mPa·s at 23° C. and 100% solids. The ester-modified polyisocyanates have an average NCO functionality of 2 to 6, preferably 2.5 to 6 and more preferably 3 to 6 and contain 5 to 20 wt. %, preferably 7 to 20 wt. % and more preferably 8 to 20 wt. % of ester groups (calculated as $C_3O_2$, MW 68); 5 to 18 wt. %, preferably 8 to 15 wt. % of isocyanate groups; and 0 to 20 wt. %, preferably of 3 to 20 wt. % and more preferably 3 to 15 wt. % of chemically incorporated hydrophilic, nonionic groups, wherein the preceding percentages are based on the solids content of the ester modified polyisocyanate.

Suitable polyisocyanates are those which have previously been described for use as component A2). The polyisocyanates have an average NCO functionality of 1.8 to 4 and an NCO content of 10 to 60, preferably of 15 to 30 wt. % and more preferably 15 to 25 wt. %, based on resin solids.

Preferred polyisocyanates B) include "lacquer polyisocyanates" based on hexamethylene diisocyanate, 1-isocyanato-3,3,5-trimethyl-5-isocyanatomethyl-cyclohexane (IPDI) and/or bis(isocyanatocyclohexyl)-methane, especially those based on hexamethylene diisocyanate. These "lacquer polyisocyanates" are known and include polyisocyanates prepared from these diisocyanates, which contain biuret, urethane, allophanate, uretdione and/or isocyanurate groups and which have been freed of surplus starting diisocyanate in known manner, preferably by distillation, such that they preferably have a residual content of less than 0.5 wt. % of unreacted diisocyanates.

The preferred lacquer polyisocyanates include polyisocyanates prepared from hexamethylene diisocyanate and containing biuret groups, such as those described in U.S. Pat. Nos. 3,124,605, 3,358,010, 3,903,126, 3,903,127 or 3,976,622. These polyisocyanates contain mixtures of N,N',N"-tris-(6-isocyanatohexyl)-biuret with lesser amounts of its higher homologs. Also preferred are polyisocyanate containing isocyanurate groups and prepared from hexamethylene diisocyanate, such as those described in U.S. Pat. No. 4,324,879. These polyisocyanates contain N,N',N"-tris-(6-isocyanatohexyl)-isocyanurate in admixture with lesser amounts of its higher homologs. Also preferred are polyisocyanates prepared from hexamethylene diisocyanate and containing mixtures of uretdione and/or isocyanurate groups, which may be obtained by the catalytic oligomerization of hexamethylene diisocyanate in the presence of trialkyl phosphine catalysts. These polyisocyanates have a viscosity at 23° C. of 50 to 500 mPa·s and an NCO functionality of 2.2 to 5.0.

Suitable polyester polyols for use in preparing polyisocyanate component B) have a number average molecular weight (determined by end group analysis) of 500 to 10,000, preferably 500 to 5000 and more preferably 750 to 3000, and a functionality of 1.8 to 6, preferably 2 to 4 and more preferably 2 to 2.5.

Suitable polyesters include those previously described for use as component A1). Preferred polyesters are hydrophobic, i.e., they do not contain component A1.d). The polyesters preferably have an acid number of less than 10, more preferably less than 5.

The use of hydrophilically-modified polyisocyanate B) is particularly recommended. The ability to emulsify the polyisocyanate into the aqueous phase is improved in this way and in some cases an additional improvement of the pot life is obtained. These hydrophilic polyisocyanates may be obtained reacting di- or polyisocyanates with monofunctional polyethers prepared from ethylene oxide and optionally propylene oxide, and/or by the incorporation of carboxylate groups by reacting di- or polyisocyanates with carboxylic acids containing hydroxyl groups, e.g., 2,2-dimethylolpropionic acid or hydroxypivalic acid, with subsequent neutralization. Suitable neutralizing agents are disclosed in U.S. Pat. No. 4,408,008, herein incorporated by reference.

Component C) is selected from carboxylate and/or sulphonate group-containing polyurethane dispersions which dry physically, are substantially free from and preferably do not contain unreacted hydroxyl groups or amino groups and are suitable for coating various substrates. Suitable dispersions are described, e.g., in DE-A 3,641,494 (U.S. Pat. No. 4,764,553, herein incorporated by reference) and DE-A 3,613,492 (U.S. Pat. No. 4,745,151, herein incorporated by reference) and in U.S. Pat. Nos. 4,066,591 and 4,408,008, herein incorporated by reference. Preferably, the aqueous dispersions of component C) have a solids content of 25 to 50 wt. %, a viscosity of 25 to 7,000, more preferably 50 to 2,500 mPa·s at 23° C. and a pH of 4 to 10, more preferably 5 to 9.

The polyurethane dispersions are preferably based on the reaction product of

C1) difunctional compounds having a number average molecular weight (which may be determined by end group analysis) of 400 to 5,000, selected from difunctional polyesters prepared from dicarboxylic acids and diols, difunctional polymers prepared from caprolactone, difunctional aliphatic polycarbonates, and/or difunctional polyethers based on propylene oxide, ethylene oxide and/or tetrahydrofuran, C2) up to 10%, based on the weight of C1), of compounds having a higher functionality, such as those previously described for use as component A1), C3) polyols, polyamines or amino alcohols having a molecular weight of 60 to 299, such as those previously described for use as component A4), C4) compounds having carboxyl or carboxylate groups and/or nonionically hydrophilic polyether groups, such as those described in the U.S. patents previously incorporated by reference, and C5) polyisocyanates containing at least two isocyanate groups and having a number average molecular weight of 140 to 1,000.

More preferably, the polyurethane dispersions have number average molecular weights of greater than 25,000; contain ammonia, triethylamine, dimethylethanol amine, N-methylmorpholine and/or dimethylisopropanolamine as neutralizing agent; have an acid number of 3 to 20, preferably 4 to 15; a minimum film formation temperature (DIN 53 767) of >10° C., preferably at least 20° C.; and contain cycloaliphatic diisocyanates as the di- or polyisocyanate component.

Solvents can also be used for the manufacture of the component C). However, the quantity of these solvents is either initially limited or subsequently reduced after mixing components A) and C), such that the resulting aqueous polyol mixture contains solvents in an amount of not more than 10 wt. %, preferably not more than 5 wt. % and more preferably not more than 3 wt. %.

To prepare the mixture of components A) and C), the aqueous solutions or dispersions of the individual components are mixed with simple stirring.

For the manufacture of the coating compositions, the invention polyisocyanate component B) is mixed with either of components A) and C) and then the remaining component is mixed or, preferably, component B) is mixed with mixture of components A) and C).

The mixing takes place by simple stirring at room temperature. The amount of the polyisocyanate component is selected to provide an NCO/OH equivalent ratio, based on the isocyanate groups of component B) and the alcoholic hydroxyl groups of component A), of 0.3:1 to 5:1, preferably 0.6:1 to 2:1. Prior to addition of the polyisocyanate component B) the known additives of lacquer technology can be incorporated into the dispersion or solution of the polyols. These additives include defoaming agents, flow-control agents, pigments and dispersion aids for pigment distribution.

The coating compositions are suitable for many areas of use in which solvent-containing, solvent-free or other types of aqueous painting and coating compositions having an enhanced range of properties are currently used, e.g., for coating various substrates composed of mineral building materials such as lime- and/or cement-bonded plasters, surfaces containing gypsum, fibrated concrete building materials and concrete; lacquering and sealing of wood and wooden materials such as particle board, wood fiber boards and paper; lacquering and coating of metallic surfaces; and coating and lacquering of asphaltic and bituminous road surfaces.

The coating compositions according to the invention are particularly suitable for the plastic substrates, particularly those used for the interior of automobiles due to the improvement in suntan lotion resistance obtained in accordance with the present invention.

The curing or cross-linking of the two-component system can take place after application to the substrate at temperatures of 0° to 200° C., preferably at room temperature.

EXAMPLES

In the following examples all parts and percentages are by weight unless otherwise indicated.

The following materials were used in the examples:

Polyisocyanate A

An isocyanurate group-containing polyisocyanate prepared from 1,6-hexamethylene diisocyanate and having an isocyanate content of 21.6%, a content of monomeric diisocyanate of <0.2% and a viscosity at 20° C. of 3000 mPa·s (available from Bayer Corporation as Desmodur N 3300).

Polyether A

A monofunctional, butanol-initiated, polyoxyethylene polyether having a molecular weight of 620.

Polyester A

A polyester diol prepared from 1,6-hexanediol, neopentyl glycol and adipic acid, number average molecular weight— 1700, molar ratio of glycols 65:35.

Polyester B

A polyester diol prepared from ethylene glycol, diethylene glycol, 1,4-butane diol and adipic acid, number average molecular weight 2000, molar ratio of glycols 0.485:0.23:0.485.

Polyester C

A polyester diol prepared from 1,6-hexanediol and adipic acid, number average molecular weight 840.

Polyester D

A polyester carbonate diol having a number average molecular weight of 2000, which is prepared by capping a polycarbonate diol prepared from 1,6-hexane diol and having a number average molecular weight of 1000 with ε-caprolactone.

Preparation of Hydroxy Ester Urethane A

A polyester polyol was initially prepared by introducing 1481 g of trimethylol propane, 5226 g of 1,6-hexanediol, 819 g of phthalic acid anhydride, 1615 g of adipic acid and 4595 g of isophthalic acid into a 15 liter reaction vessel equipped with stirrer, cooling and heating device and water separator and increasing the temperature of the reaction mixture to 250° C. for 7 hours while a stream of nitrogen was passed through. Condensation with elimination of water was continued until the polyester had a total acid number of 1.2 and an OH number of 152.

1170 g of the preceding polyester polyol, 60 g of dimethylol propionic acid and 170 g of N-methyl pyrrolidinone were weighed into a 5 liter reaction vessel equipped with stirrer and heating and cooling device, heated to 80° C. and homogenized. 1.9 g of tin(II)octoate were then added, followed by 173 g of 1,6-hexamethylene diisocyanate and the reaction mixture was stirred at 120° C. until NCO content was less than 0.05%. The resulting polyester was dispersed in a mixture of 26.7 g of dimethylethanol amine and 1850 g of demineralized water.

Hydroxy ester urethane A) had a hydroxyl number of about 80, an acid number of about 18 and a urethane group content of about 7.4% by weight, in which the preceding values are based on solids. The degree of neutralization was about 50%, the viscosity was about 1000 mPa·s at 23° C. and the solids content was about 41%.

Preparation of Hydroxy Ester Urethane B

A polyester polyol was prepared from 106 g of ethylene glycol, 146 g of 1,4-butane diol, 118 g of diethylene glycol, 70 g of trimethylol propane and 550 g of adipic acid following the procedure set forth above for preparing hydroxy ester urethane A.

Hydroxy ester urethane B) was prepared following the procedure from hydroxy ester urethane A) from 495 g of the preceding polyester polyol, 160 g of polyester D, 32 g of dimethylol propionic acid, 112 g of 1,6-hexamethylene diisocyanate, 1 g of tin(II)octoate, 182 g N-methyl pyrrolidone and 18 g of dimethylethanol amine. Hydroxy ester urethane B) had a hydroxyl number of about 62, an acid number of about 18 and a urethane group content of about 9.5% by weight, in which the preceding values are based on solids. The degree of neutralization was about 63%, the viscosity was about 20,000 mPa·s at 23° C. and the solids content was about 80%.

Preparation of Hydroxy Ester Urethane C

A polyester polyol was prepared from 532 g of 1,6-hexane diol, 56 g of neopentyl glycol, 107 g of phthalic acid, 422 g of adipic acid following the procedure set forth above for preparing hydroxy ester urethane A.

Hydroxy ester urethane C) was prepared following the procedure from hydroxy ester urethane A) from 213 g of the preceding polyester polyol, 207 g of polyester D, 22 g of dimethylol propionic acid, 16 g of trimethylol propane, 87 g of 1,6-hexamethylene diisocyanate, 1 g of tin(II)octoate, 23 g N-methyl pyrrolidone, 424 g of water and 7 g of dimethylethanol amine. Hydroxy ester urethane B) had a hydroxyl number of about 48, an acid number of about 20 and a urethane group content of about 10.7% by weight, in which the preceding values are based on solids. The degree of neutralization was about 55%, the viscosity was about 500 mPa·s at 23° C. and the solids content was about 55%.

Physically Drying Dispersion

A physically drying, aqueous polyurethane dispersion (Bayhydrol PR 340, available from Bayer Corporation) having a solids content of about 40%, a pH of about 6.5, an acid number of approx. 4 and a viscosity of about 50 mPa·s at 23° C.

Black Pigment

A black iron oxide pigment (Bayferrox 318M, available from Bayer Corporation).

Synthetic Filler

A urea methanal condensate (Pergopak M3, available from Lonza).

Wetting Agent

A polyether modified polydimethyl siloxane (Byk 346, available from Byk Chemie).

Anti-Foaming Agent

An emulsion of polysiloxane polyether copolymers (Foamex 805, available from Tego).

Light Stabilizer A

A hindered amine light stabilizer, 50% in butyl carbitol (Tinuvin 292, available from Ciba-Giegy).

Light Stabilizer B

A benzotriazole light stabilizer, 50% in butyl carbitol (Tinuvin 1130, available from Ciba-Giegy).

Solvent

Oxohexyl acetate (Exxate 600, available from Exxon).

Modified Polyisocyanates 1–6

Modified polyisocyanates 1–6 were prepared by introducing the ingredients set forth in Table 1 into a three neck round bottom flask equipped with a mechanical stirrer, thermocouple, reflux condenser, and nitrogen inlet. The mixtures were heated with stirring to 95° C. for 6 hours. The final NCO content and the viscosity of the resulting modified polyisocyanates are also set forth in Table 1.

TABLE 1

Composition of Modified polyisocyanates 1–6

| Starting Materials | Modified Polyisocyanates | | | | |
|---|---|---|---|---|---|
| | 1 (Comp) | 2 | 3 | 4 | 5 |
| Polyisocyanate A | 317.1 | 317.1 | 317.1 | 317.1 | 317.1 |
| Polyether A | 56 | 56 | 28 | 56 | 56 |
| Polyester A | | 126.9 | 87.1 | | |
| Polyester B | | | | 140.2 | |
| Polyester C | | | | | 58.8 |
| NCO Content (%) | 17.3 | 11.4 | 12.6 | 11.1 | 13.4 |
| Viscosity @ 25° C., 100% Solids (mPa · s) | 3000 | 34,000 | 40,600 | 27,320 | 14,100 |

TABLE 2

Compositions of Polyol Blends A-C

| Raw Material | Polyol Blend A | Polyol Blend B | Polyol Blend C |
|---|---|---|---|
| Physical Drying dispersion | 399.89 | 266.44 | 326.01 |
| Hydroxy ester urethane A | 195.07 | — | — |
| Hydroxy ester urethane B | — | 133.22 | — |

TABLE 2-continued

Compositions of Polyol Blends A-C

| Raw Material | Polyol Blend A | Polyol Blend B | Polyol Blend C |
| --- | --- | --- | --- |
| Hydroxy ester urethane C | — | — | 237.10 |
| Black pigment | 115.76 | 102.69 | 120.69 |
| Synthetic filler | 43.27 | 38.40 | 45.12 |
| Wetting agent | 3.14 | 2.78 | 3.28 |
| Anti-foaming agent | 5.78 | 5.12 | 6.03 |
| Light stabilizer A | 5.78 | 5.12 | 6.03 |
| Light stabilizer B | 5.78 | 5.12 | 6.03 |
| Deionized Water | 117.71 | 318.80 | 154.74 |

All materials for each polyol blend were placed in a ball mill and ground until a Hegman grind of 6+ was reached. The formulations were then filtered to remove the ceramic grinding medium.

To 100 g samples of each polyol blend were added a 50/50 mixture of Modified Polyisocyanates 1–5 (NCO:OH equivalent ratio 1.5:1) and Solvent 1. The amount set forth in Table 3 represents the total amount of polyisocyanate and solvent. The resulting compositions were mixed on a cowels disperser for 2 minutes prior to application.

TABLE 3

Coating compositions containing Modified polyisocyanates 1–5 and Polyol Blends A–C

| Isocyanate | Polyol Blend A (100 g) | Polyol Blend B (100 g) | Polyol Blend C (100 g) |
| --- | --- | --- | --- |
| Modified Isocyanate 1 | 11.03 | 9.77 | 8.99 |
| Modified Isocyanate 2 | 16.74 | 14.83 | 13.64 |
| Modified Isocyanate 3 | 15.14 | 13.41 | 12.34 |
| Modified Isocyanate 4 | 17.19 | 15.23 | 14.01 |
| Modified Isocyanate 5 | 14.24 | 12.61 | 11.61 |

The coating compositions were then applied to polycarbonate (PC) and acrylonitrile-butadiene-styrene (ABS) substrates via conventional spray equipment to a dry film thickness of 1.6 to 2.0 mils. The samples were flashed under ambient conditions for 15 minutes, baked at 75° C. for 30 minutes and then returned to ambient conditions for 1 week prior to testing.

When tested for Tg, tensile and elongation properties, chemical resistance, abrasion resistance, adhesion and water immersion, no significant differences were seen between the coatings prepared from Modified Polyisocyanates 2 to 5 (according to the invention) and Modified Polyisocyanate 1 (comparison).

The suntan lotion resistance of the coatings was also tested by placing 0.2 mL of Coppertone SPF 15 for kids suntan lotion on a 2"×2" square, spreading out the lotion and allowing it to soak in for some amount of time. The lotion was removed at specified time intervals and checked for softening or removal of the coating from the substrate. The results of this test are set forth in Tables 4 to 6.

TABLE 4

Suntan Lotion Resistance with Polyol Blend A.

| | Substrate | Time to Film Softening (hrs) | Time to Film Failure (hrs) |
| --- | --- | --- | --- |
| Modified Isocyanate 1 (Comp) | PC | 8–24 | 8–24 |
| | ABS | 8–24 | 8–24 |
| Modified Isocyanate 2 | PC | 8–24 | 8–24 |
| | ABS | 8–24 | 24–34 |
| Modified Isocyanate 3 | PC | 8 | 8–24 |
| | ABS | 8–24 | 24–34 |
| Modified Isocyanate 4 | PC | 7 | 8–24 |
| | ABS | 8–24 | 8–24 |
| Modified Isocyanate 5 | PC | 7 | 8–24 |
| | ABS | 8–24 | 8–24 |

TABLE 5

Suntan Lotion Resistance with Polyol Blend B.

| | Substrate | Time to Film Softening (hrs) | Time to Film Failure (hrs) |
| --- | --- | --- | --- |
| Modified Isocyanate 1 (Comp) | PC | 4 | 6 |
| | ABS | 8 | 8–24 |
| Modified Isocyanate 2 | PC | 8–24 | 8–24 |
| | ABS | 8–24 | 8–24 |
| Modified Isocyanate 3 | PC | 8–24 | 8–24 |
| | ABS | 8–24 | 24–34 |
| Modified Isocyanate 4 | PC | 8 | 8–24 |
| | ABS | 8–24 | 8–24 |
| Modified Isocyanate 5 | PC | 8–24 | 8–24 |
| | ABS | 8–24 | 8–24 |

TABLE 6

Suntan Lotion Resistance with Polyol Blend C

| | Substrate | Time to Film Softening (hrs) | Time to Film Failure (hrs) |
| --- | --- | --- | --- |
| Modified Isocyanate 1 (Comp) | PC | 5 | 7 |
| | ABS | 3 | 5 |
| Modified Isocyanate 2 | PC | 6 | 8 |
| | ABS | 8 | 24–34 |
| Modified Isocyanate 3 | PC | 6 | 8 |
| | ABS | 7 | 24–34 |
| Modified Isocyanate 4 | PC | 7 | 8-24 |
| | ABS | 8-24 | 8-24 |
| Modified Isocyanate 5 | PC | 5 | 7 |
| | ABS | 6 | 8-24 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. An aqueous coating composition containing prior to the reaction between components A) and B)

A) 10 to 75 wt. %, based on the solids contents of components A) and C), of at least one dispersion or solution of a polyester polyol containing carboxylate and/or sulphonate groups, having a weight average molecular weight of 1,000 to 40,000, an OH number of 15 to 100 and an acid number of 2 to 40, based on all of the carboxylate, carboxyl and sulphonate groups, B) an ester-modified polyisocyanate having an average NCO functionality of 2 to 6 and containing 5 to 20 wt.

% of ester groups (calculated as $C_3O_2$, MW 68) incorporated through polyester polyols having a functionality of 1.8 to 6, 5 to 18 wt. % of isocyanate groups and 0 to 20 wt. % of chemically incorporated hydrophilic, nonionic groups, wherein the preceding percentages are based on the solids content of the ester modified polyisocyanate and C) 25 to 90 wt. %, based on the solids contents of components A) and C), of at least one physically drying, aqueous polyurethane dispersion containing carboxylate and/or sulphonate groups, wherein components A) and B) are present at an NCO/OH equivalent ratio, based on the isocyanate groups of component B) and the hydroxyl groups of component A) of 0.3:1 to 5:1.

2. The coating composition of claim 1 wherein said ester modified polyisocyanate has an average NCO functionality of 3 to 6 and contains 7 to 20 wt. % of ester groups (calculated as $C_3O_2$, MW 68) based on the solids content of the ester modified polyisocyanate.

3. The coating composition of claim 1 wherein said ester-modified polyisocyanate is water dispersible and contains 3 to 20 wt. % of chemically incorporated hydrophilic, nonionic groups based on the solids content of the ester modified polyisocyanate.

4. The coating composition of claim 2 wherein said ester modified polyisocyanate is water dispersible and contains 3 to 20 wt. % of chemically incorporated hydrophilic, nonionic groups based on the solids content of the ester modified polyisocyanate.

5. An aqueous coating composition containing prior to the reaction between components A) and B)

A) 10 to 75 wt. %, based on the solids contents of components A) and C), of at least one dispersion or solution of a polyester polyol containing carboxylate and/or sulphonate groups, having a weight average molecular weight of 1,000 to 40,000, a urethane group content of 2.5 to 15 wt. %, based on the solids content of component A), an OH number of 15 to 100 and an acid number of 2 to 40, based on all of the carboxylate, carboxyl and sulphonate groups, B) an ester-modified polyisocyanate having an average NCO functionality of 2 to 6 and containing 5 to 20 wt. % of ester groups (calculated as $C_3O_2$, MW 68) incorporated through polyester polyols having a functionality of 1.8 to 6, 5 to 18 wt. % of isocyanate groups and 0 to 20 wt. % of chemically incorporated hydrophilic, nonionic groups, wherein the preceding percentages are based on the solids content of the ester modified polyisocyanate and C) 25 to 90 wt. %, based on the solids contents of components A) and C), of at least one physically drying, aqueous polyurethane dispersion containing carboxylate and/or sulphonate groups, wherein components A) and B) are present at an NCO/OH equivalent ratio based on the isocyanate groups of component B) and the hydroxyl groups of component A) of 0.3:1 to 5:1.

6. The coating composition of claim 5 wherein said ester modified polyisocyanate has an average NCO functionality of 3 to 6 and contains 7 to 20 wt. % of ester groups (calculated as $C_3O_2$, MW 68) based on the solids content of the ester modified polyisocyanate.

7. The coating composition of claim 5 wherein said ester modified polyisocyanate is water dispersible and contains 3 to 20 wt. % of chemically incorporated hydrophilic, nonionic groups based on the solids content of the ester modified polyisocyanate.

8. The coating composition of claim 6 wherein said ester modified polyisocyanate is water dispersible and contains 3 to 20 wt. % of chemically incorporated hydrophilic, nonionic groups based on the solids content of the ester modified polyisocyanate.

* * * * *